United States Patent [19]
Buscemi et al.

[11] Patent Number: 5,690,682
[45] Date of Patent: Nov. 25, 1997

[54] DEVICE AND METHOD FOR TREATMENT OF CARDIAC ARRHYTHMIA

[75] Inventors: Paul J. Buscemi, Long Lake; Brian Jackson, Mound; Stan Obino, Edina, all of Minn.; Robert Arzbaecher, Chicago, Ill.

[73] Assignee: PharmaTarget, Inc., Minneapolis, Minn.

[21] Appl. No.: 666,889

[22] Filed: Jun. 17, 1996

[51] Int. Cl.$^6$ ............................................. A61M 5/20
[52] U.S. Cl. ................................ 607/3; 604/890.1
[58] Field of Search ..................... 607/3; 604/890.1, 604/841.1, 892.1, 247, 248

[56] References Cited

U.S. PATENT DOCUMENTS

| | | |
|---|---|---|
| 3,692,027 | 9/1972 | Ellinwood, Jr. . |
| 4,003,379 | 1/1977 | Ellinwood, Jr. . |
| 4,146,029 | 3/1979 | Ellinwood, Jr. . |
| 4,557,724 | 12/1985 | Gregonis et al. . |
| 5,042,497 | 8/1991 | Shapland . |
| 5,220,917 | 6/1993 | Cammilli et al. . |
| 5,224,938 | 7/1993 | Fenton, Jr. ............... 604/247 |
| 5,305,745 | 4/1994 | Zacouto . |
| 5,306,293 | 4/1994 | Zacouto . |
| 5,527,344 | 6/1996 | Arzbaecher et al. ......... 607/3 |
| 5,545,205 | 8/1996 | Schulte et al. ............ 607/123 |

Primary Examiner—Scott Getzow
Attorney, Agent, or Firm—Vidas, Arrett & Steinkraus, P.A.

[57] ABSTRACT

An implantable programmable drug delivery system for injection of a pharmaceutical agent into the peritoneum to treat cardiac arrhythmia is described. The device consists of essentially three components: a main body containing electronics, power supply, valve means, and drug reservoir; an electronic lead into the heart to transmit impulses from the heart and deliver electronic responses to the heart; and a separate specialized drug delivery catheter for delivery of agents to the peritoneal cavity or near the exterior of the pericardium.

19 Claims, 5 Drawing Sheets

DEVICE AND METHOD FOR TREATMENT OF CARDIAC ARRHYTHMIA

BACKGROUND OF THE INVENTION

1. Field of the Invention

The present invention relates generally to implantable medical devices, and more particularly to such devices adapted to deliver pharmaceutical agents to the peritoneum or thorax in the vicinity of the heart to correct arrhythmias of the heart.

2. Description of the Related Art

Implantable medical devices for converting arrhythmias of the heart to sinus rhythm have typically relied on the use of electrical energy and/or the delivery of pharmaceutical agents to the heart. U.S. Pat. Nos. 3,692,027, 4,003,379, 4,146,029, 5,220,917 provide examples of such previously proposed devices. Typically, these devices deliver the electrical or pharmaceutical therapy directly to the heart or the vasculature. U.S. Pat. No. 5,042,497 to Shapland discloses a system to predict and prevent arrhythmias in combination with an implanted arrhythmia treatment device. The system triggers the implanted arrhythmia treatment device to take preventative and curative actions such as applying an anti-arrhythmia drug to the heart of a patient.

Still other implantable medical devices have been developed. For example, U.S. Pat. No. 5,305,745 to Zacouto discloses an implantable device that has means for the automatic measurement of biological parameters of the blood (particularly pertaining to hemodynamics, the myocardium, the arteries, or components present in the blood), implanted observation means, threshold means for comparing the parameter measured value, and means which automatically deliver a suitable treatment, for example a fibrinolytic treatment. The device also relates to fibrillations and tachycardias, but only intervenes with a cardiac shock if the condition is very serious or persisting, and can optionally deliver drugs into the blood stream based on measured blood parameters and heart conditions. U.S. Pat. No. 5,306,293 also to Zacouta describes a similar intelligent device to prevent cardiac failures by administering treatments such as drugs into the blood stream or into the myocardium.

U.S. Pat. No. 4,557,724, issued to Gregonis et al., discusses the advantages of delivering drugs or solutions to the peritoneal cavity, which has been used as a dialysis site since the 1920s and continues to be used for peritoneal dialysis to treat patients with end-stage renal disease. The Gregonis refillable device is for administering insulin and includes the use of hydrogels as a surface coating or in combination with a base polymer to minimize cellular adhesion and accumulation.

Although the prior art implantable devices make decisions based on sensed heart conditions to initiate drug delivery, the devices deliver drugs directly into to the heart or to the vascular system. There exists a need for an intelligent feedback device to administer drugs to the body based on sensed cardiac conditions without direct connection to the heart. The peritoneum has been proven to be a favorable site for dialysis and for delivering insulin, but it is not known in the art to deliver anti-arrhythmic or defibrillation drugs to the peritoneum based on sensed heart conditions. Particular classes and forms of anti-arrhythmic drugs exist which require very low blood concentrations for prolonged periods of time to be effective. These low concentrations can be difficult to obtain by direct infusion of the drug into the vasculature. The present invention overcomes this problem by providing an implantable device and method for delivering anti-arrhythmic drugs directly into either the peritoneal or thorax cavity of the body to provide and maintain low blood concentrations of anti-arrhythmic drugs. Furthermore, the present device also allows for the delivery of carrier bound anti-arrhythmic drugs that would not be tolerated by the vasculature.

SUMMARY OF THE INVENTION

The present invention provides a programmable drug delivery system with a housing and catheters which are adapted to be implanted in the human body with the catheters inserted into the heart and the peritoneal or the thorax cavity adjacent to the heart for use to correct arrhythmias of the heart, which system provides for delivery of forms of anti-arrhythmic drugs not suitable for delivery directly into the cardiovascular system.

According to the present invention there is provided a system including (1) a housing capable of being implanted in the human body; (2) electronic control means including electrical connection means for analyzing electrical signals of the type produced by the heart received through the electrical connection means, for identifying signals indicating the onset of arrhythmia in the heart, and for providing electrical energy to the heart through the connection means to effect sinus rhythm of the heart (e.g., to pace the heart) in response to a signal from the analyzing means indicating a predetermined condition in the heart requiring application of such electrical energy; (3) pump means within the housing for supplying under pressure through an outlet opening an anti-arrhythmic drug capable of treating the tissues of the heart in response to a signal from the analyzing means indicating the onset of arrhythmia of the heart; and (4) first and second catheters.

The first catheter comprises an elongate body having a liquid lumen extending longitudinally within the body from an inlet end at a proximal end of the body to an outlet port spaced between the proximal end and a distal end of the body. Valve means are provided on the body at the outlet port of the lumen to afford movement of liquid under pressure in the liquid lumen out through the outlet port and for preventing movement of liquid around the peripheral surface into the outlet port. The proximal end of the body of the first catheter is attached to the housing of the system with the inlet opening of the liquid lumen in communication with the outlet opening of the pump means.

The second catheter comprises an elongate body, at least one electrode on its peripheral surface connected by an electrical lead extend longitudinally within the body to contact end of the leads at the proximal end of the body. The electrode is at or adjacent the distal end of the body to afford positioning the catheter in the heart with the electrode in the apex of the right ventricle chamber. The proximal end of the body of the second catheter is attached to the housing of the system with the contact end of the electrical lead in electrical connection with the electrical input connection so that the electronic means receives signals through the electrode, and the electrical energy to the heart is provided through the electrode.

Thus, when coupled to the first and second catheters, the system can receive and monitor electrical signals of the type produced by the heart, supply under pressure a liquid chemical capable of treating the tissues of the heart to treat the arrhythmia when a signal from the analyzing means indicates the onset of arrhythmia of the heart, and provide electrical energy to the heart to effect its sinus rhythm (e.g., to pace the heart) in response to a signal from the analyzing means indicating that such electrical treatment is needed.

Different numbers and locations of electrodes on the second catheter can be used to provide the electrical signals to the electronic means. When only one electrode is used on the second catheter, the electronic means can receive signals sensed between the electrode at or adjacent its distal end and the housing to monitor activities in the right ventricle. Alternatively, three electrodes can be used to monitor the activity of the heart wherein first, second, and third electrodes are located on the peripheral surface connected by first, second, and third electrical leads extending longitudinally within the body to contact ends of the leads at the proximal end of the body. The first electrode is at or adjacent the distal end to the body and the second and third electrodes are spaced longitudinally along its peripheral surface from its distal end to afford positioning the catheter in the heart with the first electrode in the apex of the right ventricle chamber and the second and third electrodes in the right atrium chamber or a major vein of the heart connected to the right atrium chamber. The proximal end to the body of the second catheter is attached to the main body of the system with the contact ends of the electrical leads in electrical connection with the electrical input connection so that the electronic means receives signals through the first, second, and third electrodes, and the electrical energy to the heart is provided through the first electrode. When only first, second, and third electrodes are used on the second catheter, the electronic means can receive signals sensed between the second and third electronic means can receive signals sensed between the second and third electrodes to monitor the activity of the right atrium chamber of the heart, and between the first electrode at or adjacent its distal end and the housing to monitor the activities in the right ventricle chamber of the heart. Alternatively, the distal end of the second catheter can be inserted into the coronary sinus of the heart to monitor the activity of the left atrium or the left ventricle.

Preferably the outlet port of the liquid lumen opens through the peripheral surface of the body of the first catheter at a location that will be in the peritoneal cavity adjacent to the small intestines. The valve means at that outlet opening can comprise an enclosure of resiliently elastic material tensioned around and fixed along the peripheral surface over the outlet port and adapted to be resiliently flexed by pressure applied through liquid in the lumen to afford movement of liquid through that outlet port and between the peripheral surface and the enclosure.

The elongated body of the catheter can have a longitudinally extending stylet passageway that is adapted to receive a stylet for stiffening and shaping the catheter during its insertion into the body.

Also, means adapted for securing the body of the second catheter within the heart may be provided such as an electrically conductive means attached and electrically connected to the first electrode and adapted to be embedded in the tissues of the heart, or non-conductive means attached to the body adjacent its distal end adapted to engage with the tissues of the heart.

The system can also include a liquid reservoir in the main body adapted to contain the liquid chemical from which the supply means supplies the anti-arrhythmic drug, and means on the main body for affording injection of the anti-arrhythmic drug into the liquid reservoir.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
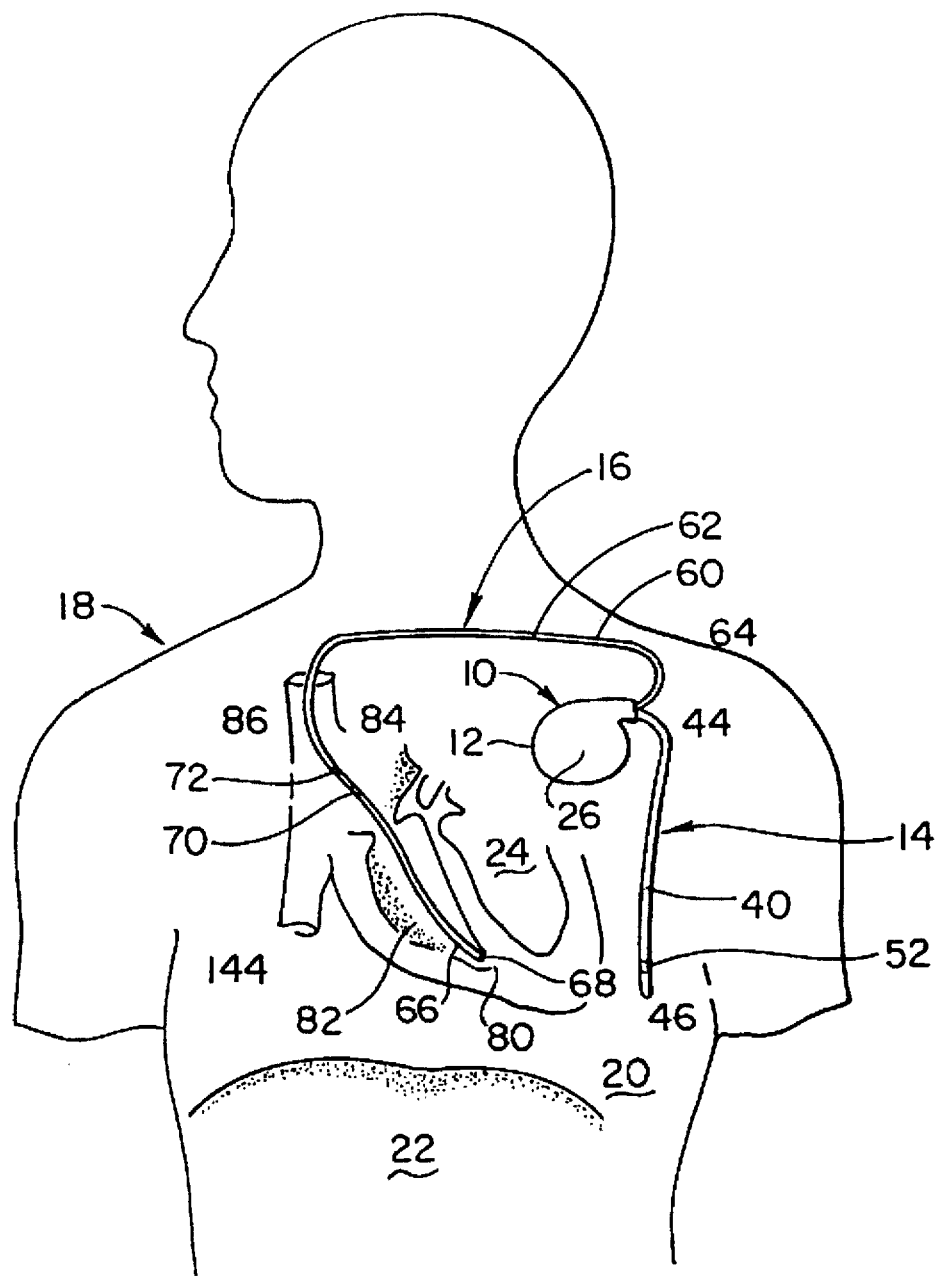
FIG. 1 is a side view of a first embodiment of a medical device and catheters according to the present invention shown with a portion of the first catheter inserted into a human heart from which portions have been removed to show details and a portion of the second catheter inserted into a human thorax cavity adjacent to the human heart from which portions have been removed to show details.
Figure 2:
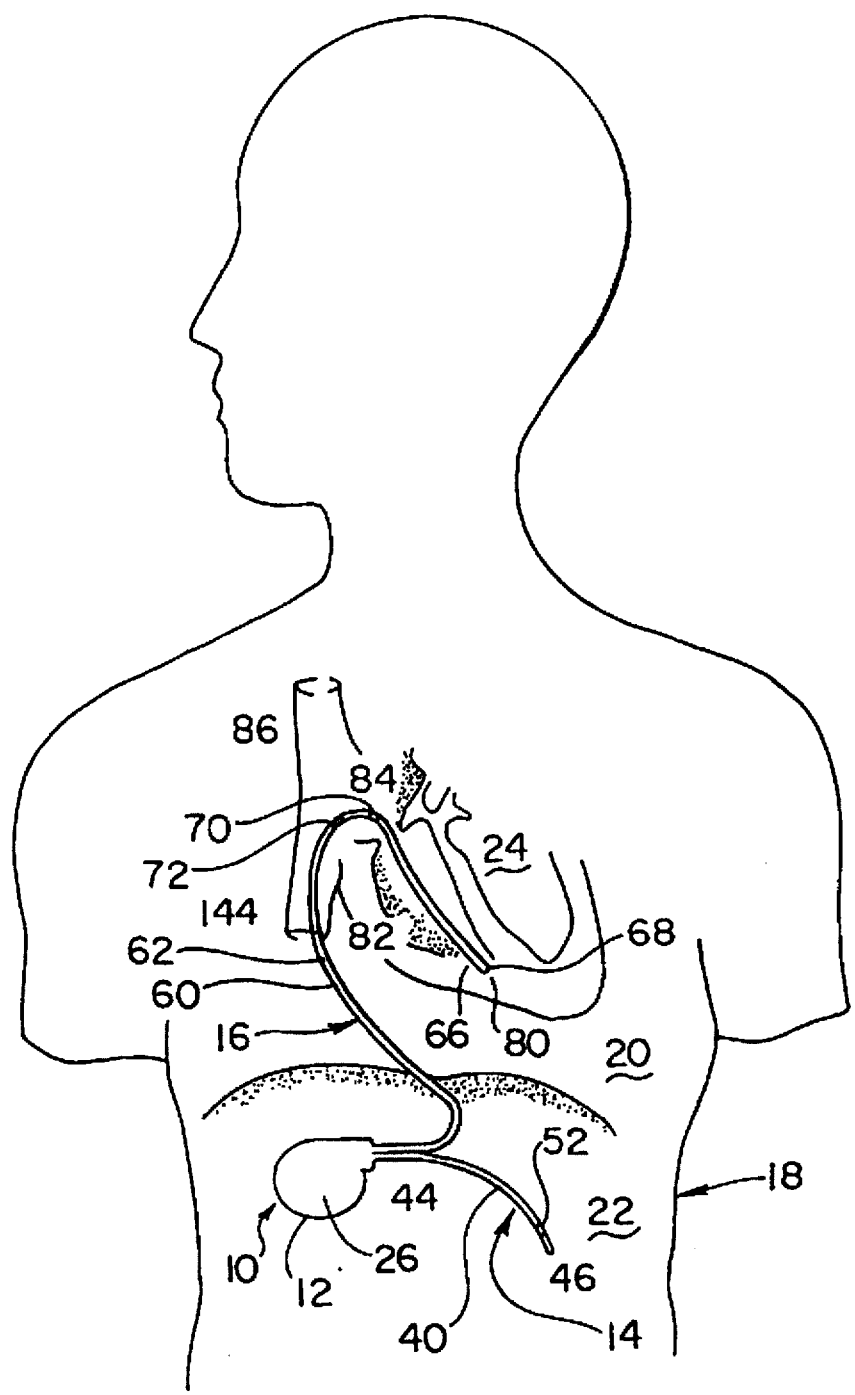
FIG. 2 is a side view of a first embodiment of a medical device and catheters according to the present invention shown with a portion of the first catheter inserted into a human heart from which portions have been removed to show details and a portion of the second catheter inserted into a human peritoneal cavity from which portions have been removed to show details.
Figure 6:
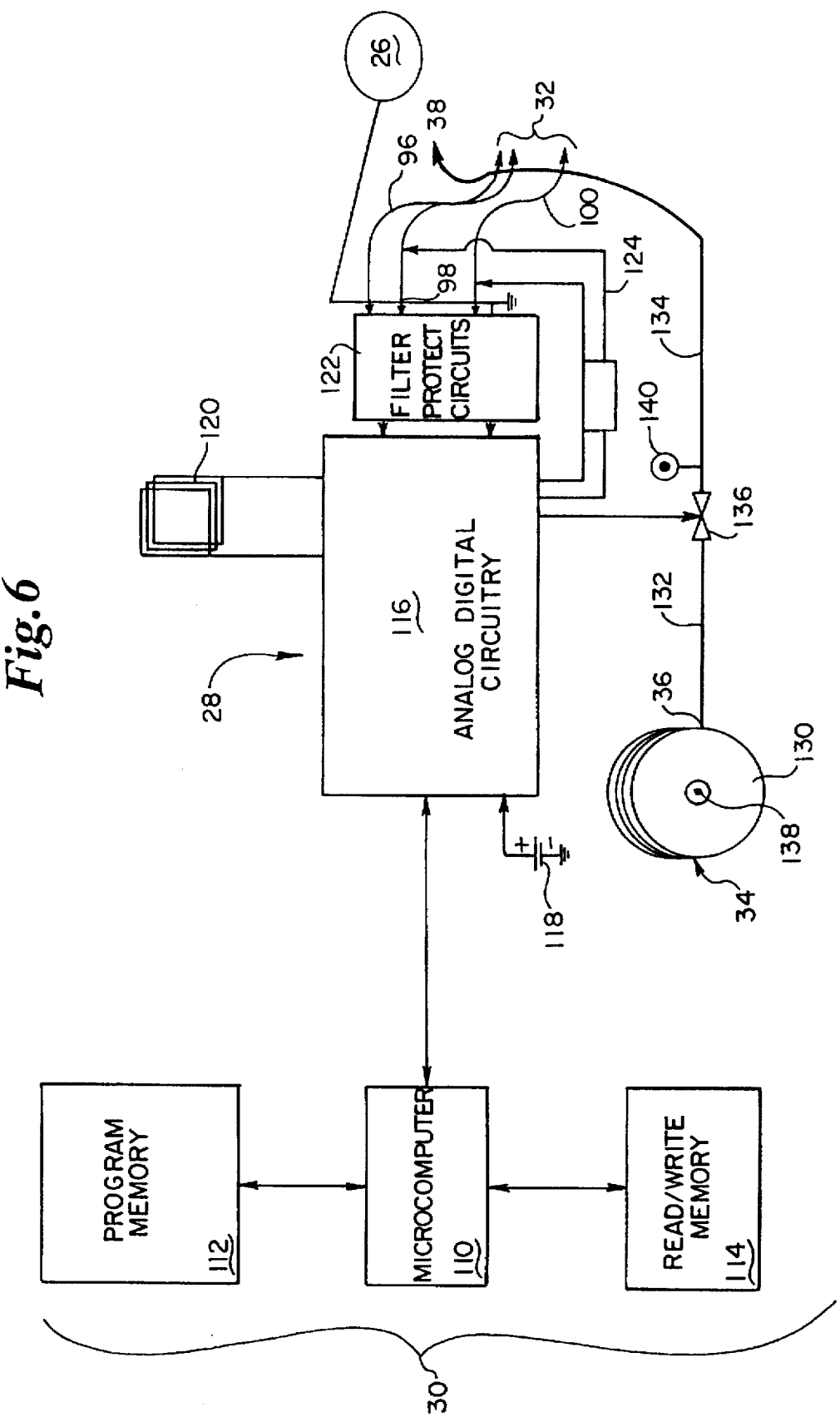
FIG. 6 is a schematic view of electronic means and liquid chemical supply means included in the medical device of FIG. 1.

Referring now to the FIGS. 1 and 6 of the drawings, there is shown a first embodiment of an assembly 10 according to the present invention which comprises a medical device 12 and first and second catheters 14 and 16. The assembly 10 is adapted to be implanted in a human body 18 with a portion of the first catheter 14 inserted into the thorax cavity 20 (FIG. 1 ) or the peritoneal cavity 22 (FIG. 2) of the body 18 and a portion of the second catheter 16 inserted into a heart 24 within the body 18.

Generally, the medical device 12 comprises a housing 26 which contains electronic means 28 (FIG. 6) including analyzing means 30 for analyzing electrical signals of the type produced by the heart 24 received through electrical connection means 32, for identifying signals indicating the onset of arrhythmia in the heart 24, and can provide electrical energy to the heart through the electrical connection means 32 to pace the heart 24 in response to a signal from the analyzing means 30 indication a predetermined condition in the heart 24; and supply means 34 within the housing 26 having an output port 36 for supplying under pressure through the outlet opening 38 a liquid chemical capable of treating the tissues of the heart 24 in response to a signal from the analyzing means 30 indicating the onset of arrhythmia of the heart 24.

Figure 4:
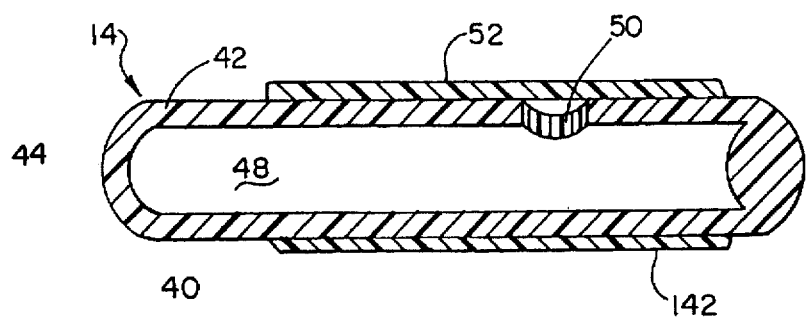
FIG. 4 is an enlarged cross sectional view taken approximately along lines 4—4 of FIG. 3 showing the one-way fluid check valve.

As can be seen in FIG. 4, the first catheter 14 comprises an elongate body 40 having a peripheral surface 42, proximal and distal ends 44 and 46, and a liquid lumen 48 extending longitudinally in the elongated body 40 from an inlet end at its proximal end 44 to an outlet port 50 between its proximal and distal ends 44 and 46. The outlet port 50 is spaced longitudinally along the peripheral surface 42 adjacent the distal end 46, as illustrated, to afford positioning the first catheter 14 in either the thorax 20 or the peritoneal cavity 22 with the outlet port 50 in the thorax 20 adjacent to the heart 24 or the peritoneal cavity 22 adjacent to the small intestines (not shown). Valve means 52 on the elongate body 40 at the outlet port 50 afford movement of liquid under pressure in the liquid lumen 48 out through the outlet port 50 and prevent movement of liquid or blood around the peripheral surface 42 of the elongated body 40 into the outlet port 50.

Figure 5:
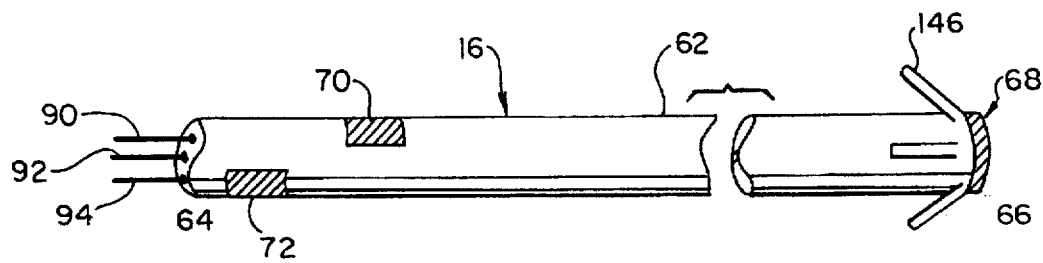
FIG. 5 is a view of the electronic/receiver module, sensing catheter lead and drug delivery port.

As can be seen in FIG. 5, the second catheter 16 comprises an elongate body 60 having a peripheral surface 62, proximal and distal ends 64 and 66. First, second, and third electrically conductive electrodes 68, 70, and 72 are attached on the peripheral surface 62 of the elongated body 60. The first electrode 68 is a blunt tip electrode at or adjacent the distal end 66, whereas the second and third electrodes 70 and 72 are semi-cylindrical electrodes partially encircling and disposed on opposite sides of the peripheral surface 62 of the elongated body 60. The electrode configuration is believed to provide a larger and more discrete electrical signal from the heart 24 and are described in more detail in U.S. Pat. No. 5,127,403 the content of which patent is hereby incorporated herein by reference in its entirety.

The second and third electrodes 70 and 72 are spaced apart (i.e., in the range of 5 to 20 millimeters) and are spaced longitudinally along the peripheral surface 62 from the distal end 66 by distances (i.e., in the range of 11 to 16 centimeters) that afford positioning the second catheter 16 in the heart 24 with the first electrode 68 in the apex 80 of its right ventricle chamber 82 and the second and third electrodes in its right atrium chamber 84 as is illustrated in FIG. 1, or with the second and third electrodes in the superior vena cava vein 86 of the heart 24 that is connected with the right atrium chamber 84. First, second, and third electrical leads 90, 92 and 94 extend longitudinally within the elongated body 60 from contact ends (not shown) at its proximal end 64 to the first, second, and third electrodes 68, 70 and 72, respectively.

The proximal end 44 of the first catheter 14 is releasably attached to the medical device 12 with the inlet opening of the liquid lumen 48 in communication with the outlet opening 38 of the medical device 12 (not shown). The proximal end 64 of the second catheter 16 is also releasably attached to the medical device 12 with the contact ends of the electrical leads 90, 92 and 94 in electrical connection with electrical input connections 96, 98, and 100 (see FIG. 6) for the electronic means 28 so that the electronic means 28 receives bipolar signals from the right atrium chamber 84 of the heart 24 between the second and third electrodes 70 and 72 and unipolar signals from the right ventricle chamber 82 of the heart 24 between the first electrode 68 and the housing 26. The analyzing means 30 for analyzing electrical signals of the type produced by the heart 24 received through electrical connection means 32, for identifying signals indicating the onset of arrhythmia in the heart 24, and can provide electrical energy to the heart through the electrical connection means 32 to pace the heart 24 in response to a signal from the analyzing means 30 indicating a predetermined condition in the heart 24 comprises a microcomputer 110 to which is coupled a program memory 112 that stores the control program that analyzes signals from the heart 24 to determine arrhythmia of the heart 24 and determines when to supply electrical energy to the heart through the electrical connection means 32 to effect sinus rhythm of the heart, and a read/write memory 114 that is programmable to afford setting of parameters, and which stores history of electrical impulses received from the heart. The microcomputer 110 is coupled to custom analog and digital circuitry 116 through which power is supplied by a depletable power supply or battery 118 and through which it is connected to a telemetry antenna 120 through which provided to or received from the read/write memory 114. The electrical input connections 96, 98, and 100 are connected to the custom analog and digital circuitry 116 through filters and high voltage protection circuits 122 that protect the electronic means 28 from destructive electrical inputs such as could result from defibrillation of the heart by electrical impulses. A line 124 through which the electronic means can provide electrical energy to the heart to effect sinus rhythm of the heart 24 is connected around the filters and high voltage protection circuits 122 between the custom analog and digital circuitry 116 and the electrical input connection 96. Such electrical energy to the heart 24 paces the heart 24 in a unipolar modality.

The supply means 34 within the housing 26 having an output port 36 for supplying under pressure through the outlet opening 38 a liquid chemical capable of treating the tissues of the heart 24 in response to a signal from the analyzing means 30 indicating the onset of arrhythmia of the heart 24 comprises a pressurized chamber 130 (i.e., a container divided by a flexible diaphragm, one side of which is stored an inert gas under pressure, and on the other side of which is stored the liquid chemical). The liquid containing portion of the pressurized chamber is connected by lines 132 and 134 through a valve 136 to the outlet opening 38 which is coupled to the inlet opening of the liquid lumen 48 of the first catheter 14. The valve 136 is controlled between open and closed conditions by the microcomputer 110 with the custom analog and digital circuitry 116. The pressurized chamber is adapted to be filled through the use of a self-sealing septum 138 or other coupling means on the housing 26 of the medical device 12. The septum 138 may be constructed from any flexible polymer material including silicon rubber. A flush port 140 is connected to the line 134, and can be used to purge the liquid lumen 48 of the first catheter 14. The housing 26 of the medical device 12 is constructed of biocompatable materials, such as titanium, or 316 stainless steel.

As can be seen in FIG. 4, the valve means 52 at the outlet port 50 is provided by a cylindrical band 142 of resiliently elastic material tensioned around and fixed to the elongated body 40 of the first catheter 14 along one edge so that the cylindrical band 142 extends over the outlet port 50. The cylindrical band 142 is adapted to be resiliently flexed by pressure applied thought the liquid in the lumen 48 to afford movement of liquid through the outlet port 50 and between the elongated body 40 and the cylindrical band 142. The elastic cylindrical band 142 may be constructed from a variety of rubber materials such as silicone rubber or polyurethane.

Liquid chemicals capable of treating the tissues of the heart 24 that can be dispensed by the assembly 10 include, but are not limited to, quinine, disopyramide, procainamide, lidocaine, mexiletine, encainide, flecainide, propafenone, propanolol, nadolol, metrorolol, atenolol, amiodarone, sotalol, clofilium, dofetilide, ibutilide, verapamil, and diltiazem. The assembly 10 can also dispense the liquid chemicals bound in solid polymeric matrix structures.

First and second catheters 14 and 16 are releasably attached to and can be separated from the medical device 12 to facilitate inserting the first catheter 14 into either the thorax 20 or peritoneal cavity 22 and the second catheter 16 into the heart 24. The first catheter 14 is inserted either into the thorax 20 to position the valve means 52 adjacent to the heart 24 or the peritoneal cavity 22 to position the valve means 52 adjacent to the small intestines (not shown). The proximal end 44 of the first catheter 14 is then attached to the medical device 12. The proximal end 44 of the catheter 14 and a portion of the medical device 12 are adapted to seal together to thereby couple the inlet opening to the liquid lumen 48 in the first catheter 14 with the outlet opening 38 of the medical device 12. The second catheter 16 is releasably attached to and can be separated from the medical device 12 facilitate inserting it into the heart 24 of the human body. The catheter 16 is inserted into the heart 24 transvenously through a cephalic or subclavian vein (not shown) or the inferior vena cava 144 to position its distal tip 66 at the apex of the right ventricle 80. The proximal end 64 of the catheter 16 is then attached to the medical device 12. The proximal end 64 of the catheter 16 and a portion of the medical device 12 are adapted to seal together to thereby engaging the contact ends on the electrical leads 90, 92, and 94 with the electrical input connections 96, 98, and 100 of the medical device 12. The medical device 12 of the attached assembly 10 is then positioned subcutaneously within the human body.

The elongated body of the first and second catheters 14 and 16 can be made by extrusion of an implantable polyurethane, silicone rubber or other implantable flexible biocompatable polymer. The electrical leads 90, 92, and 94 can be made of MP35N alloy, or other commonly used electrical lead metal. The electrodes 68, 70 and 72 can be made of implantable metal such as platinum/iridium alloys, or other commonly used electrode metal (e.g., stainless steel).

The first and second catheters 14 and 16 each have a stylet passageway (not shown) extending longitudinally in its elongated body 40 and 60 from an inlet end (not shown) located at the proximal end 36 to the distal tip. The stylet passageway is adapted to receive a guide stylet for stiffening trod shaping the catheters 14 and 16 during insertion of the catheters 14 and 16 into the body 18 and the heart 24.

Figure 3:
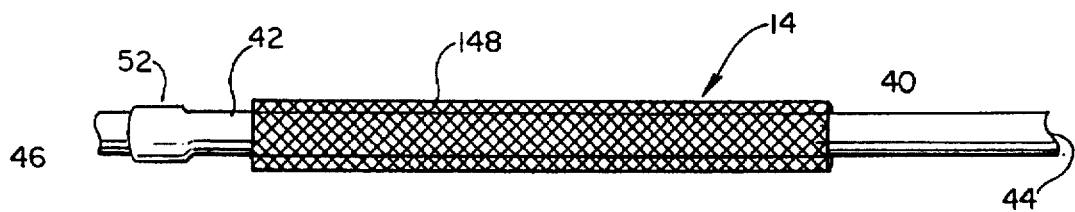
FIG. 3 is a fragmentary view of an end portion of the first catheter that can be used in an assembly of a medical device according to the present invention.

The assembly includes means for securing the elongated body 60 of the second catheter within the heart 24. The elongated body 60 includes four circumferentially spaced tines 146 near the distal end 66 of the catheter 16 that project both radially away from the periphery of the elongated body 60 and toward its proximal end 64. The tines afford passive fixation of the distal end 66 in the apex of the right ventricle 80 by engaging with the endocardial surface of the heart 24. Alternatively, the electrode 68 could include a helical corkscrew like projection adapted to be screwed into the tissue of the right ventricle 82 by rotating the elongated body 60 after its insertion into the heart 24 to anchor the catheter 16 in the heart 24 tissues. Attachment of the first catheter 14 to tissue of the body 18 may be by simple adhesion, which maybe accomplished by adding a treatment to the first catheter 14 to allow in-growth, such as a polyethylene terepthalate mesh 148 as shown in FIG. 3.

Figure 7:
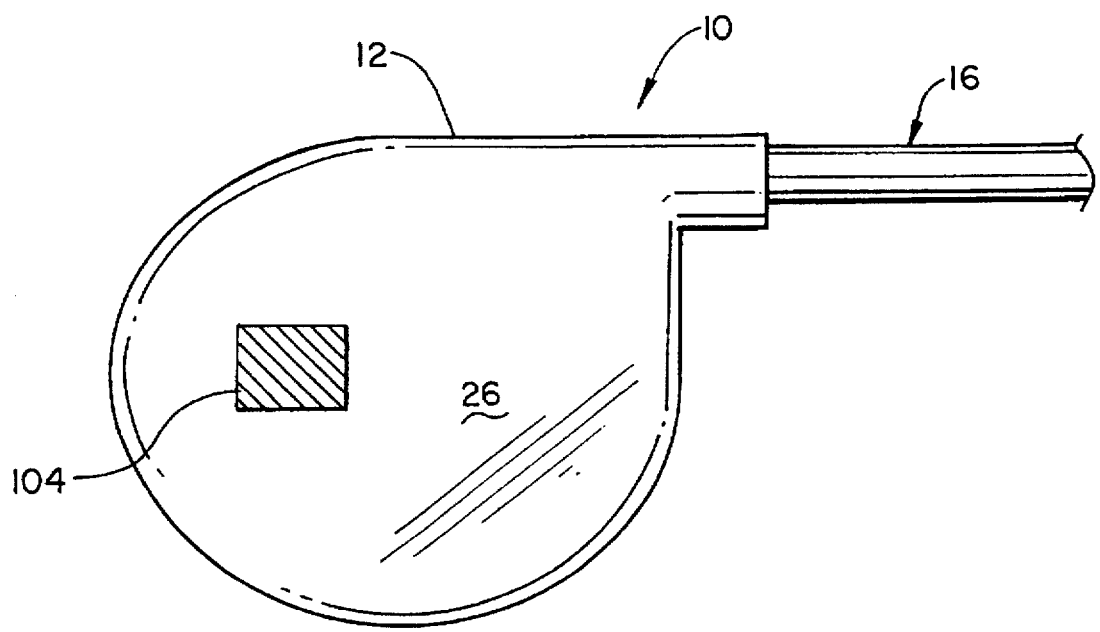
FIG. 7 is a side view of a second embodiment of a medical device and catheters according to the present invention.

Referring now to FIG. 7 there is illustrated a second embodiment of a medical device 12 that can be used in an assembly of a medical device and catheters according to the present invention. The medical device 12 has a surface valve means 104 on the surface of the housing 26 of the assembly. Liquid chemicals are dispensed through an opening in the housing surface via surface valve means 104.

The present invention has now been described with reference to two embodiments thereof. It will be apparent to those skilled in the art that many changes and modifications can be made in the embodiments described without departing from the scope of the present invention. For example electrodes 68, 70 and 72 may be cylindrical encircling the peripheral surface 34 of the elongated body 32. Thus the scope of the present invention should not be limited to the structures described in this application, but only by structures described by the language of the claims and the equivalents of those structures.

What is claimed is:

1. A programmable drug delivery system, said system comprising:
   (a) a housing capable of being implanted in the human body, said human body having a heart with atrial and ventricular chambers, and a peritoneal and thoracic cavity;
   (b) electronic means within the housing including electrical connection means and means for analyzing electrical signals of the type produced by the heart received through said electrical connection means, for identifying signals indicating the onset of arrhythmia in the heart, and for providing electrical energy to the heart through the connection means to effect sinus rhythm of the heart in response to a signal from said analyzing means indicating a predetermined condition of the heart;
   (c) a rechargeable reservoir means within the housing having an outlet opening for supplying under pressure through the outlet opening a liquid chemical capable of treating the tissues of the heart in response to a signal from said analyzing means indicating the onset of arrhythmia of the heart;
   (d) a first catheter, said first catheter comprising an elongate body having a peripheral surface, proximal and distal ends, a liquid lumen extending longitudinally in said body from an inlet end at said proximal end to an outlet port between said proximal and distal ends, valve means on said elongate body at said outlet port for affording movement of liquid under pressure in said liquid lumen out through said outlet port, said distal end adapted for positioning within the peritoneal cavity or the thorax cavity, adjacent the heart, and said first catheter including attachment means for attaching the first catheter to tissue in the peritoneal cavity or in the thorax cavity adjacent the heart; and
   (e) a second catheter, said second catheter comprising an elongate body having a peripheral surface, an electrode on said peripheral surface, said electrode being at or adjacent said distal end to afford positioning the catheter in the heart, and an electrical lead extending longitudinally within said body from contact ends at said proximal end to said electrode;
   the proximal end of said first catheter elongate body being attached to the housing with the contact end of said electrical lead being coupled to said electrical connection means so that the electronic means receives signals through said electrode, and the electrical energy to the heart is provided through said electrode.

2. The programmable drug delivery system of claim 1 wherein said second catheter further includes second and third electrodes on said peripheral surface, and second and third electrical leads extending longitudinally within said body from a contact end at said proximal end to said second and third electrodes, said second and third electrode being spaced apart and spaced longitudinally along said peripheral surface from said electrode to afford positioning the catheter in the heart with said electrode in the apex of the right ventricle chamber and said second and third electrodes in one of the right atrium chamber or a major vein of the heart connected to the right atrium chamber, the contact ends of said electrical leads being adapted for electrical connection with said connection means so that the electronic means receives signals between said second and third electrodes.

3. The programmable drug delivery system of claim 1 wherein said second catheter is adapted for positioning within the heart with said electrode in the coronary sinus or on the surface of the right atrium of the heart.

4. The programmable drug delivery system of claim 1 wherein said distal tip of said first catheter is adapted for positioning within the peritoneal cavity, said peritoneal cavity having small intestines, such that the valve means are positioned adjacent to the small intestines.

5. The programmable drug delivery system of claim 1 wherein said attachment means for attaching the peripheral surface of the first catheter to the tissue in the peritoneal cavity or in the thorax cavity adjacent the heart includes covering the peripheral surface of said first catheter with a woven fiber structure adjacent and proximal to the valve means.

6. The programmable drug delivery system of claim 1 wherein said outlet port of said liquid lumen of the first catheter opens through said peripheral surface at a position spaced longitudinally along said peripheral surface from said distal end of said body to afford positioning said catheter in the peritoneal cavity or the thorax cavity of the human body with said distal end of said elongate body adjacent to the small intestines or the pericardium of the heart, and said valve means comprises an enclosure of resiliently elastic material tensioned around and fixed along said peripheral surface over said outlet port and adapted to be resiliently flexed by pressure applied through liquid in said lumen to afford movement of liquid through said outlet port and between said peripheral surface and said enclosure.

7. The programmable drug delivery system of claim 1 wherein said elongate body of first and second catheters have a stylet passageway extending longitudinally in said body from an inlet end at said proximal end, said stylet passageway being adapted to receive a styler for stiffening and shaping the catheter during insertion of the catheter.

8. The programmable drug delivery system of claim 1 wherein said second catheter further including means adapted for securing the body within the heart.

9. A catheter according to claim 8 wherein said means adapted for securing the body within the heart comprises electrically conductive means attached and electrically connected to said first electrode and adapted to be embedded in the tissues of the heart.

10. A catheter according to claim 8 wherein said means adapted for securing the body within the heart comprises means attached to said body adjacent said distal end adapted to engage with the tissues of the heart.

11. The programmable drug delivery system of claim 1 wherein said electrodes of the second catheter are semi-annular and partially encircle the peripheral surface of the body.

12. The programmable drug delivery system of claim 1 wherein said first catheter comprises a liquid delivery means on the surface of the housing of the programmable drug delivery system.

13. A method for infusing liquid chemical agents directly into the peritoneal or thorax cavity of a human for the purpose of converting an arrhythmia of the heart to sinus rhythm, said method comprising the steps of:

sensing a series of electrical signals produced by the functioning of the heart;

analyzing the electrical signals sensed in said sensing step to identify signals indicating the onset of arrhythmia;

injecting into the peritoneal or thorax cavity a liquid chemical capable of converting the arrhythmia to sinus rhythm in response to the identification of signals indicating the onset of arrhythmia in said analyzing step; and applying electrical energy to the tissues of the heart to pace the heart after said injection step.

14. A method according to claim 13 further including the steps of providing a housing, and implanting the housing beneath the skin of the humans' body, and wherein said sensing step comprises the step of providing an electrical lead having a sensing end adapted to receive the series of electric signals produced by the functioning of the heart and an opposite end positioned in said housing, and the step of implanting the sensing end of the lead in the tissues of the heart;

said analyzing step comprises the step of providing electronic circuitry in said housing and in electrical contact with the opposite end of the electrical lead for analyzing the signals sensed in said sensing step and for sequentially producing first and second output signals in response to identifying signals indicating the onset of arrhythmia;

said injecting step comprises the step of providing a pumping assembly coupled to the electronic circuitry and adapted to be activated upon receipt of the first output signal, said pump assembly including pump means in the housing having an inlet and an outlet opening for pumping the liquid chemical received through the inlet opening out of the outlet opening under pressure upon activation of the pumping assembly, a supply of the liquid chemical in the housing and communicating with the inlet opening; and a liquid lead having inlet and outlet ends and a through opening between said inlet and outlet ends, the inlet end being coupled to the pump with the outlet opening communicating with the through opening, and an injection valve having inlet and outlet ends and a through opening between said inlet and outlet ends with the inlet end of the valve being attached to the outlet end of catheter with the through openings in communication, and the step of implanting the outlet end of the nozzle in the tissues and the blood contained within the heart; and said applying step comprises the step of providing in the housing a source of electrical energy and control means connected to the electronic circuitry for connecting the source of electrical energy to the opposite end of the electrical connecting the source of the electrical lead upon receipt of the second output signal to apply the electrical energy to the tissues of the heart through the electrical lead.

15. An implantable, programmable drug delivery system for injection of a pharmaceutical agent into the peritoneum or thorax adjacent the heart to treat cardiac arrhythmia, said system comprising:

(a) a main body including a rechargeable reservoir for a pharmaceutical agent to be injected, said reservoir including an outlet, said main body further including a power supply, pump means and electronic control means;

(b) a flexible first catheter for injecting the pharmaceutical agent which is constructed and arranged to extend from the outlet of said reservoir to the peritoneum or thorax adjacent to the heart of a patient, said first catheter including attachment means for attaching the first catheter to tissue in the peritoneum or thorax adjacent the heart and further including a valve means to regulate flow through said first catheter;

(c) a second catheter adapted for positioning within the heart including means for determining the state of circulation;

(d) arrhythmia detection means for receiving and interpreting the signal transmitted by said means for determining the state of circulation, to enable arrhythmia to be detected; and (e) means for injecting the pharmaceutical agent from said reservoir via said flexible catheter at a predetermined pressure, and activated by the arrhythmia detection means on detection of arrhythmia.

16. The drug delivery system of claim 15 wherein said first catheter has a surface treatment that causes the rapid and permanent adhesion of the catheter to the pericardium through the interaction of the modified surface of the catheter.

17. A method for treating arrhythmia or fibrillation in a patient in need of such treatment, the method comprising the steps of:

(a) implanting an intelligent feedback device into a patient, said device including a main body which includes a rechargeable reservoir for supplying a pharmaceutical agent, a power supply and electronic control means including a sensing catheter, and a flexible catheter for delivering said agent; said flexible catheter including a distal end and a proximal end, the proximal end being in fluid communication with said reservoir;

(b) inserting said sensing catheter to the heart such that it may sense conditions within the heart and send signals to the heart; and (c) attaching the distal end of said flexible catheter to tissue in the thorax adjacent the heart such that agents may be delivered in response to said electronic control means outside of the circulatory system for a controlled diffusion into the circulatory system.

18. A method for treating arrhythmia or fibrillation in a patient in need of such treatment, the method comprising the steps of:

(a) implanting an intelligent feedback device into a patient, said device including a main body which includes a rechargeable reservoir for supplying a pharmaceutical agent, a power supply and electronic control means including a sensing catheter; and a flexible catheter for delivering said agent; said flexible catheter including a distal end and a proximal end, the proximal end being in fluid communication with said reservoir;

(b) inserting said sensing catheter to the heart such that it may sense conditions within the heart and send signals to the heart; and (c) attaching the distal end of said flexible catheter to tissue in the peritoneal cavity such that agents may be delivered in response to said electronic control means outside of the circulatory system for a controlled diffusion into the circulatory system.

19. The method of claim 18 wherein said distal end of said flexible catheter is attached to tissue adjacent the small intestine of said patient and the distal end of said sensing catheter is located in the apex of the right ventricle, the coronary sinus or the right atrium of the heart.

* * * * *